United States Patent
Raghavan et al.

(10) Patent No.: US 8,406,850 B2
(45) Date of Patent: Mar. 26, 2013

(54) METHOD FOR ESTIMATING THE PHYSIOLOGICAL PARAMETERS DEFINING THE EDEMA INDUCED UPON INFUSION OF FLUID FROM AN INTRAPARENCHYMALLY PLACED CATHETER

(75) Inventors: Raghu Raghavan, Baltimore, MD (US); Martin Brady, Monkton, MD (US)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 13/241,936

(22) Filed: Sep. 23, 2011

(65) Prior Publication Data

US 2012/0046538 A1    Feb. 23, 2012

Related U.S. Application Data

(63) Continuation of application No. 12/121,103, filed on May 15, 2008, now abandoned.

(30) Foreign Application Priority Data

May 16, 2007  (EP) .................................... 07108374
May 7, 2008   (EP) .................................... 08155788

(51) Int. Cl.
    *A61B 5/05*   (2006.01)
(52) U.S. Cl. ........................................ 600/410
(58) Field of Classification Search .............. None
    See application file for complete search history.

(56) References Cited

U.S. PATENT DOCUMENTS

| | | | |
|---|---|---|---|
| 5,720,720 A | 2/1998 | Laske et al. | |
| 6,026,316 A | 2/2000 | Kucharczyk et al. | |
| 2005/0007100 A1* | 1/2005 | Basser et al. ................. | 324/200 |

FOREIGN PATENT DOCUMENTS

| | | |
|---|---|---|
| WO | 00/07652 | 2/2000 |
| WO | 2006/035443 | 4/2006 |

OTHER PUBLICATIONS

Morrison et al. Focal delivery during direct infusion to brain: role of flow rate, catheter diameter, and tissue mechanics, AJP—Regu Physiol, Oct. 1, 1999 vol. 277 No. 4 R1218-R1229.*
Sarntinoranont et al. Computational Model of Interstitial Transport in the Spinal Cord using Diffusion Tensor Imaging, Jul. 2006, Annals of Biomedical Engineering, vol. 34, No. 8, pp. 1304-1321.*
Chen et al. Variables affecting convection-enhanced delivery to the striatum: a systematic examination of rate of infusion, cannula size, infusate concentration, and tissue-cannula sealing time, J. Neurosurg. / vol. 90 / Feb. 1999.*

(Continued)

*Primary Examiner* — Long V. Le
*Assistant Examiner* — Bo J Peng
(74) *Attorney, Agent, or Firm* — Renner, Otto, Boisselle & Sklar, LLP (57) ABSTRACT

A method for estimating the physiological parameters defining the edema induced upon infusion of fluid from an intraparenchymally placed catheter including; a) acquisition of patient-specific medical data; b) estimation of pertinent tissue microstructure based on the patient-specific medical data and/or generalized information derived or drawn from one or more of the following: experience, literature, modeling, studies, research, analysis; c) acquisition of information about delivery parameters, and/or delivery device geometry, and/or fluid properties; and d) computing a field of values of predicted extracellular volume fraction over the tissue region using the information obtained in (b) and (c). According to a further aspect, a method of infusing or planning and/or monitoring an infusion of a contrast agent such that the distribution of such agent can be detected and observing and/or measuring the backflow length along the catheter track.

17 Claims, 11 Drawing Sheets

Fig08, pore fraction estimated from image vs pore fraction simulated/computed

OTHER PUBLICATIONS

Kaczmarek et al. The hydromechanics of hydrocephalus: steady state solution for cylindrical geometry, Bulletin of Mathematical Biology, vol. 59, No. 2, pp. 295-323, 1997.*

Basser et al. Diffusion-tensor MRI: theory, experimental design and data analysis—a technical review, NMR Biomed. 2002;15:456-467.*

Zhang et al. Interstitial hydraulic conductivity in a fibrosarcoma, Am J Physiol Heart Circ Physiol 279: H2726-H2734, 2000.*

Brady et al. Quantifying Fluid Infusions and Tissue Expansion in Brain, IEEE Transactions on Biomedical Engineering, vol. 58, No. 8, Aug. 2011.*

Raghavan et al. Predictive models for pressure-driven fluid infusions into brain parenchyma, Phys. Med. Biol. 56 (2011) 6179-6204.*

Supplemental European Search Report dated May 18, 2010 for European Application No. 08155788.6.

Chen et al., "Biphasic Finite Element Model of Solute Transport for Direct Infusion into Nervous Tissue", Annals of Biomedical Engineering, vol. 35, No. 12, Dec. 2007, pp. 2145-2158.

Mardor et al., "Convection-Enhanced Drug Delivery: Increased Efficacy and Magnetic Resonance Image Monitoring", Cancer Research, American Association for Cancer Research, vol. 65, No. 15, Aug. 2005, pp. 6858-6863.

Morrison et al., "Focal delivery during direct infusion to brain: role of flow rate, catheter diameter, and tissue mechanics", American Journal of Physiology: Regulatory, Integrative and Comparative Physiology, American Physiological Society, vol. 277, No. 4, Jan. 1999, pp. R1218-R1229.

Sarntinoranont et al., "Computational Model of Interstitial Transport in Spinal Cord using Diffusion Tensor Imaging", Annals of Biomedical Engineering, vol. 34, No. 8, Jul. 2006, pp. 1304-1321.

Smith et al., "Modeling Convection Enhanced Delivery in Brain: Fluid and Mass Transport Analyses", 9th AIAA/ASME Joint Thermophysics and Heat Transfer Conference Proceedings, vol. 1, No. 5, Jun. 2006, pp. 301-311.

* cited by examiner

METHOD FOR ESTIMATING THE PHYSIOLOGICAL PARAMETERS DEFINING THE EDEMA INDUCED UPON INFUSION OF FLUID FROM AN INTRAPARENCHYMALLY PLACED CATHETER

RELATED APPLICATION DATA

This application is a continuation of application Ser. No. 12/121,103 filed on May 15, 2008 now abandoned, the contents of which is hereby incorporated by reference in its entirety.

FIELD OF THE INVENTION

This invention relates to the field of convection-enhanced drug delivery (see U.S. Pat. No. 5,720,720) and estimates the expansion of tissue upon pumping of an infusate into the tissue.

BACKGROUND

In convection-enhanced delivery of drugs in solution into brain parenchyma in particular, the expansion or edema of the tissue is one of the most important determinants of the distribution of the infusate. The extracellular volume fraction of tissue can rise from a nominal 0.2 to 0.7 or so. This very dramatic increase in the fraction of fluid containing extracellular space can increase the hydraulic conductivity by orders of magnitude, thus directing flow of fluid into such edematous spaces in favor of other channels which are much more restricted because of smaller relative extracellular volume.

It is thus important to predict which regions of tissue, in particular brain tissue, are expanded and by how much, for given flow rates of infusate. As important as predicting the volumes of the nervous system that would readily expand, is to actually predict those places that cannot expand due to anatomic or physiological reasons. Those places that cannot expand would likely act as a barrier to fluid flow since other regions around them may become more conducive to the fluid flow.

SUMMARY OF THE INVENTION

The present invention provides anatomic-based methods to predict expansion coefficients in different regions of tissue.

The present invention as specified in this description and, in particular, as defined by the appended claims, affords advantages over prior art methodologies. A method according to the invention may comprise any of the features herein disclosed, and any sensible combination of one or more of such features.

For moderate infusion rates (less than 5 microliters per minute for example), the grey matter regions of the brain do not show edema, while the major white matter tracts away from the corpus callosum do show edema. This invention makes such knowledge more quantitative, and defines the expected extracellular space under such conditions of infusion.

For the special application of delivering cells to tissue, it has long been the question where cells would stop migration and settle down. The information about the presence of crossing nerve fibers could be used to deduce and compute those locations and hence be able to estimate the pathway and target of cell migration. The information generated thereby can be relevant for cellular treatments of any kind, including the treatment with stem cells, and including the development and execution of therapies for neoplastic and neurodegenerative diseases as well as epilepsy.

Similarly, the information can be used to derive the migration pathways and the target of viruses or viral vectors present within or delivered to tissue. For example, the treatment of Progressive Multifocal Leukoencephalopathy, an infection of the brain that occurs primarily in immunosupressed patients, may be significantly improved since from a visible lesion the presences of other likely masses of virus can be predicted.

Another useful embodiment of the invention includes the simulation of not only the migration of tumor cells, but more importantly their location of settlement. For example, brain tumor cells choose the white matter as their routes of distribution within the brain, causing distant recurrences of tumor. The information about the presence of fiber crossings can enhance the existing view to add the points of cancer cell settlement, allowing for a pre-emptive strike against the now foreseeable locations of recurrent tumor.

Especially in terms of identifying locations of tumor recurrence, speed of migration and space play important roles. Speed of migration, as described above, can be deduced by knowing the locations of blockages for migrations. The available space can be computed by using image processing methods such as those herein described, especially extracting the resting pore fraction from the images.

Knowing the resting pore fractions and being able to predict and manage them is another important factor in the treatment of many different diseases. For example, in brain tumors or multiple sclerosis, a disruption of the blood-brain-barrier results in a local increase of interstitial pressure and hence in the formation of edema (swelling) around the volumes that are affected by the disease. By combining medication that attacks the disease with medication that globally or locally reduces the swelling of the brain, one can manage the therapeutic effect of an infused agent for medication, while also actively influencing any spreading and/or settling of the disease in distant volumes and locations.

Figure 1:
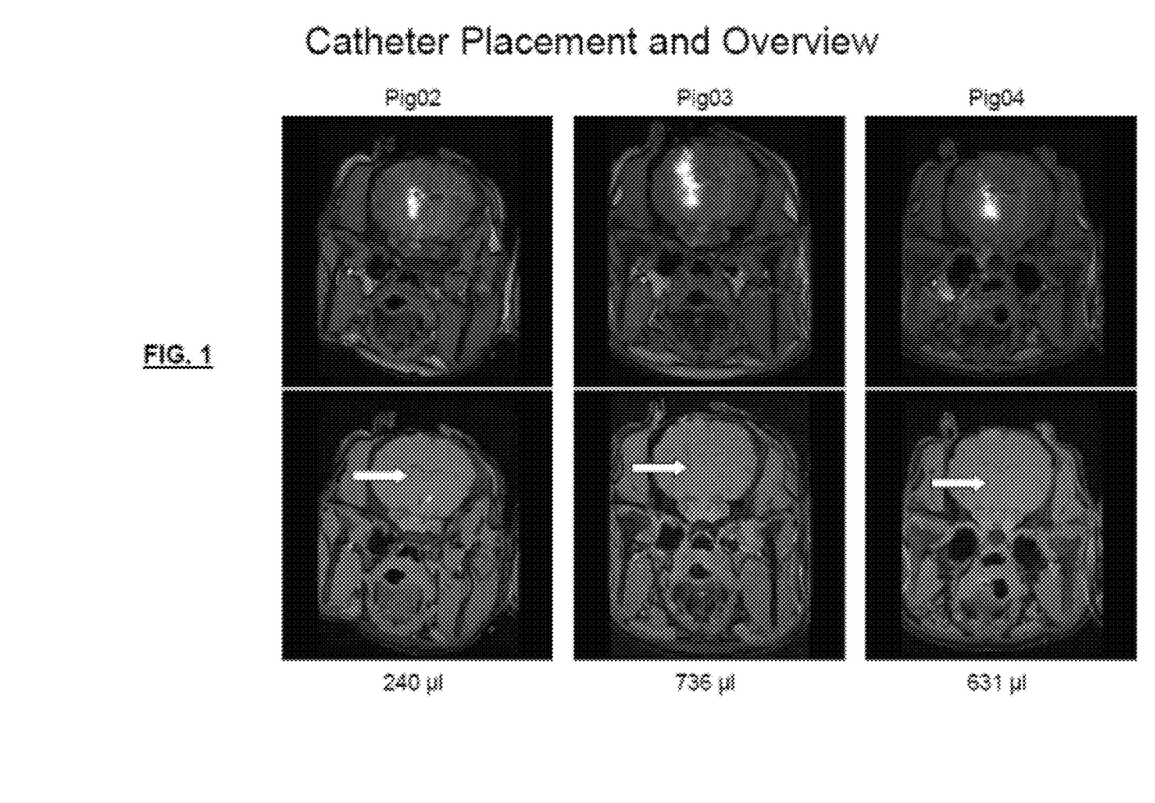
FIG. 1 shows in the upper row a MRI T1w image showing an infusion of contrast agent (Gd DTPA) in three different amounts into the brains of three pigs. It is visible that the distribution is very heterogeneous, and that fluid flows back along the catheter track. Also, parts of the infused fluid flow around and into the ventricular system of the pig brains. In the lower row, white arrows indicate catheter positioning in the three pigs.
Figure 2:
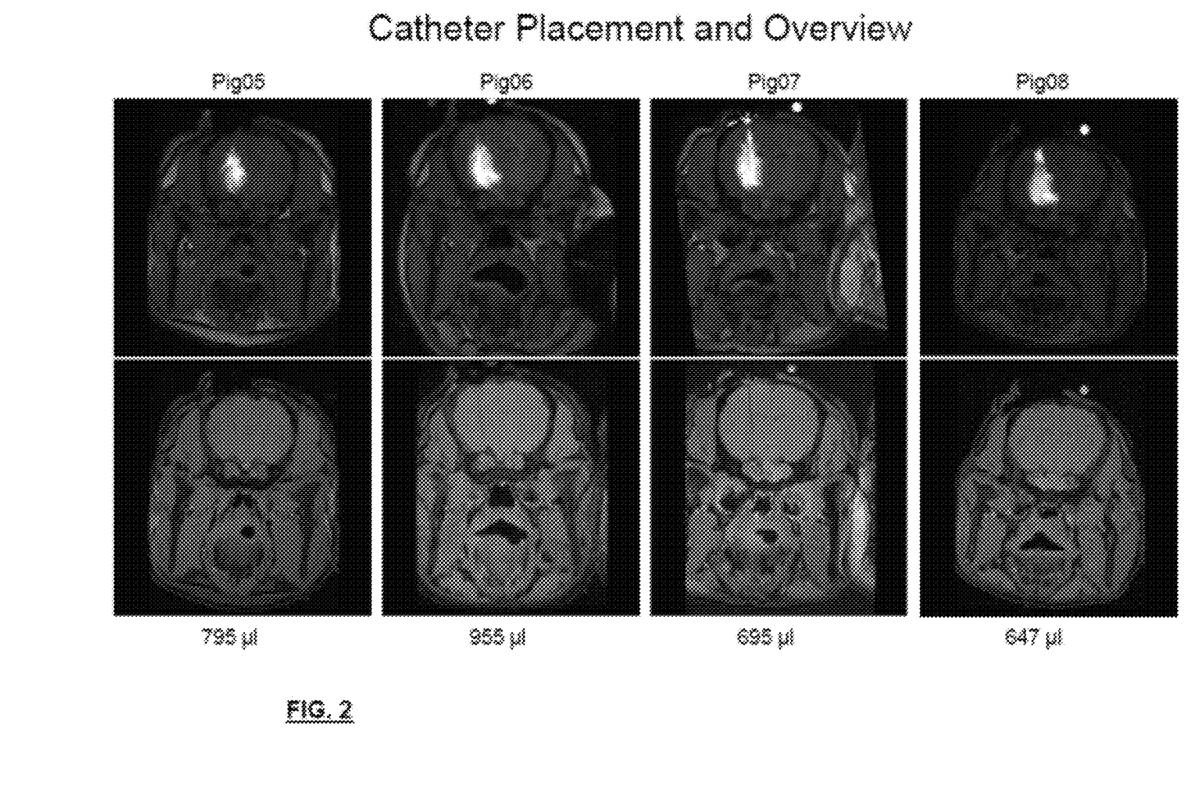
FIG. 2 shows in the upper row a MRI T1w image showing an infusion of contrast agent (Gd DTPA) in four different amounts into the brains of four pigs. It is apparent that the distribution is very heterogeneous, and that fluid flows back along the catheter track. Also, parts of the infused fluid flow around and into the ventricular system of the pig brains. In the lower row, white arrows indicate catheter positioning in the four pigs.
Figure 3:
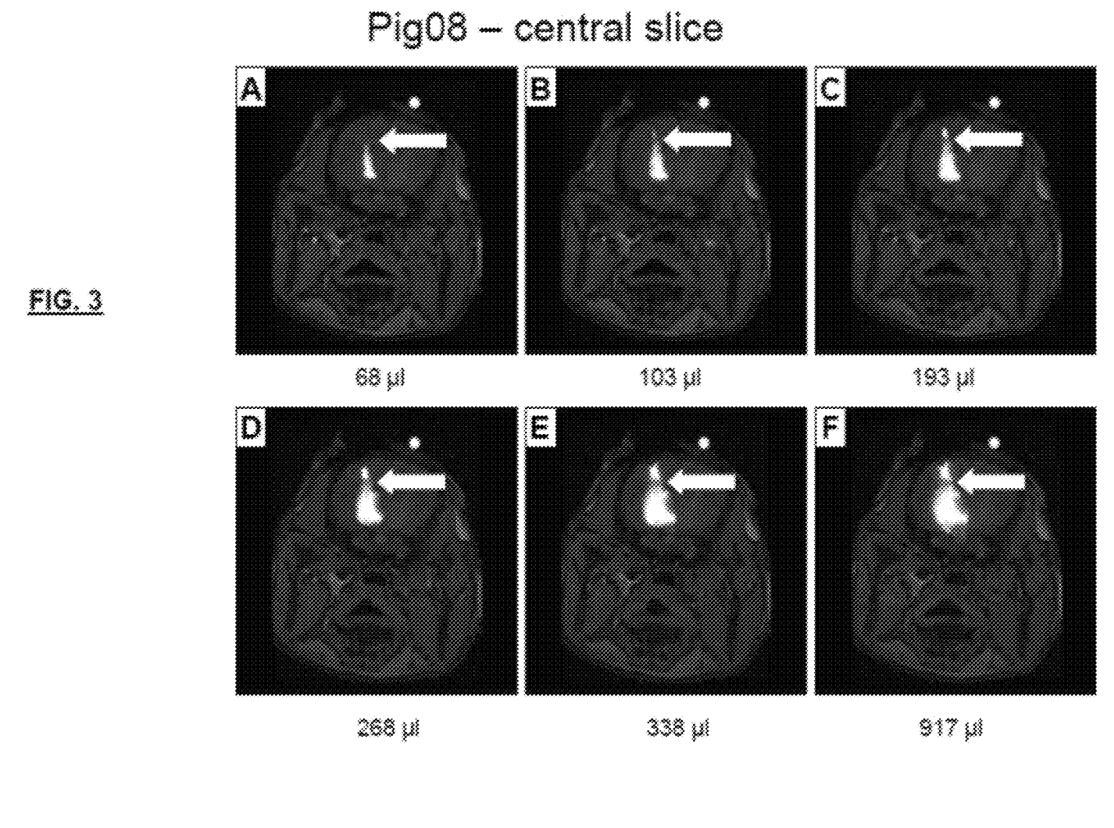
FIG. 3 shows a MRI slice of infusion into one pig at various time points into the infusion (respective volumes infused given below the pictures). Dim areas in the distribution indicate regions that are not expanded by the infused fluid and act as a barrier or "bottleneck" for the infusion (indicated by white arrow). In particular, it is to be noted that in FIG. 3A the point that does not expand at the following
Figure 4:
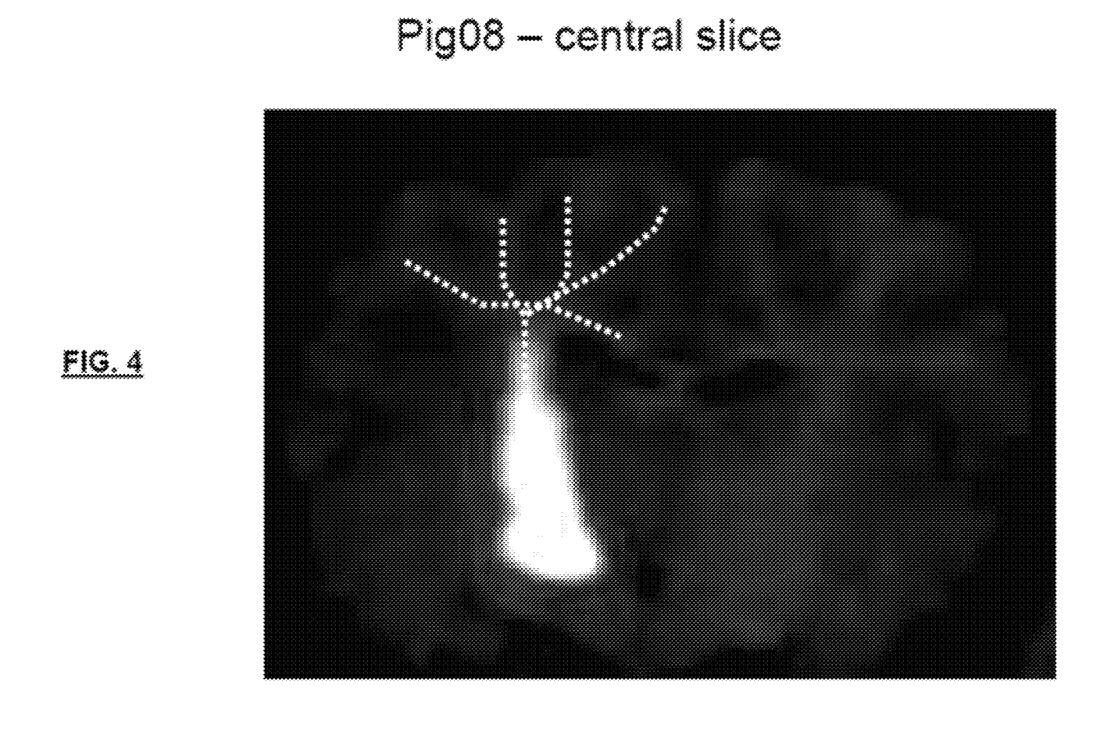
FIG. 4 is an enlargement of FIG. 3A. The dotted lines represent the nerve fiber tracks visible on the MR T1w image. Various tracks cross at the point that is unexpandable by the infused fluid.
Figure 5:
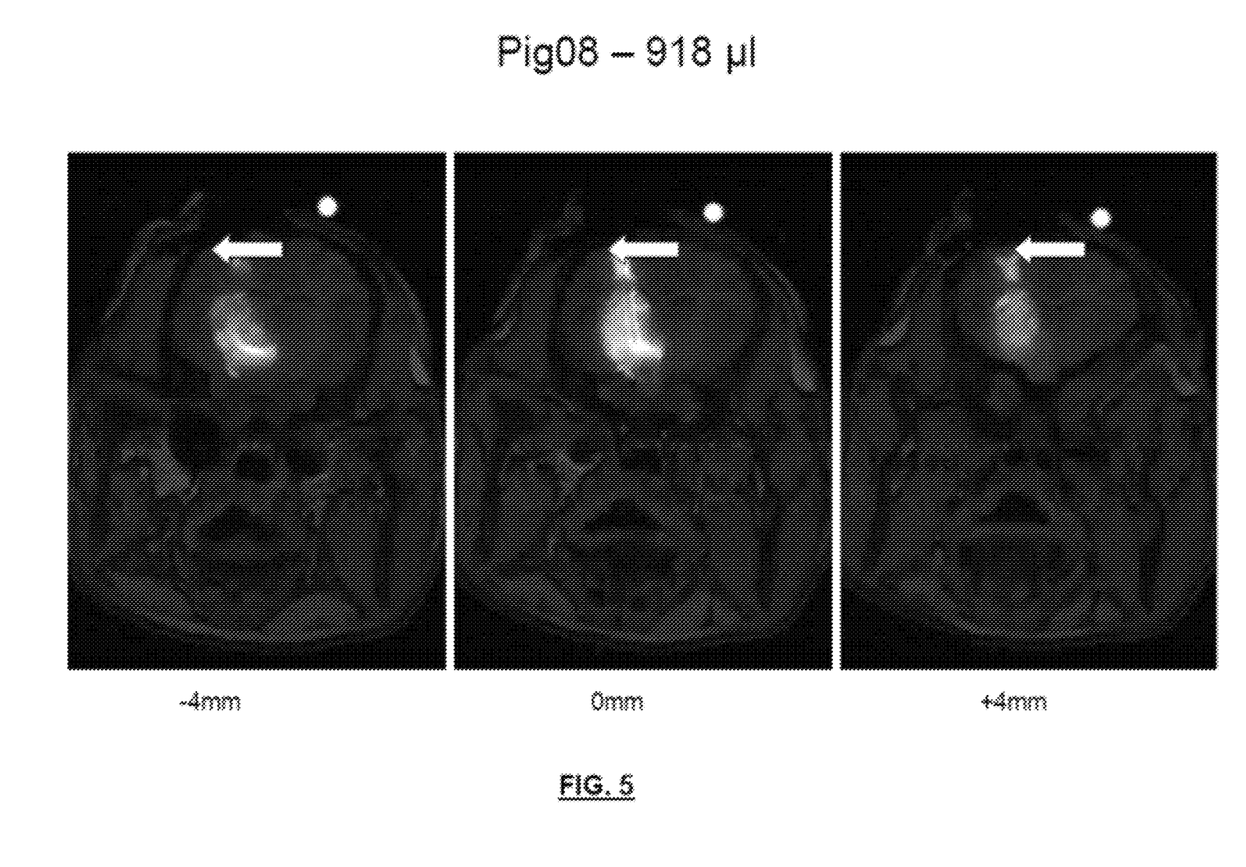
FIG. 5 shows various slices of the same infusion time point in one pig. It is observable that the fiber crossing, although it does not expand, is still conducive to fluid flow. There is significant contrast agent distribution beyond the crossing (indicated by the white arrow).
Figure 6:
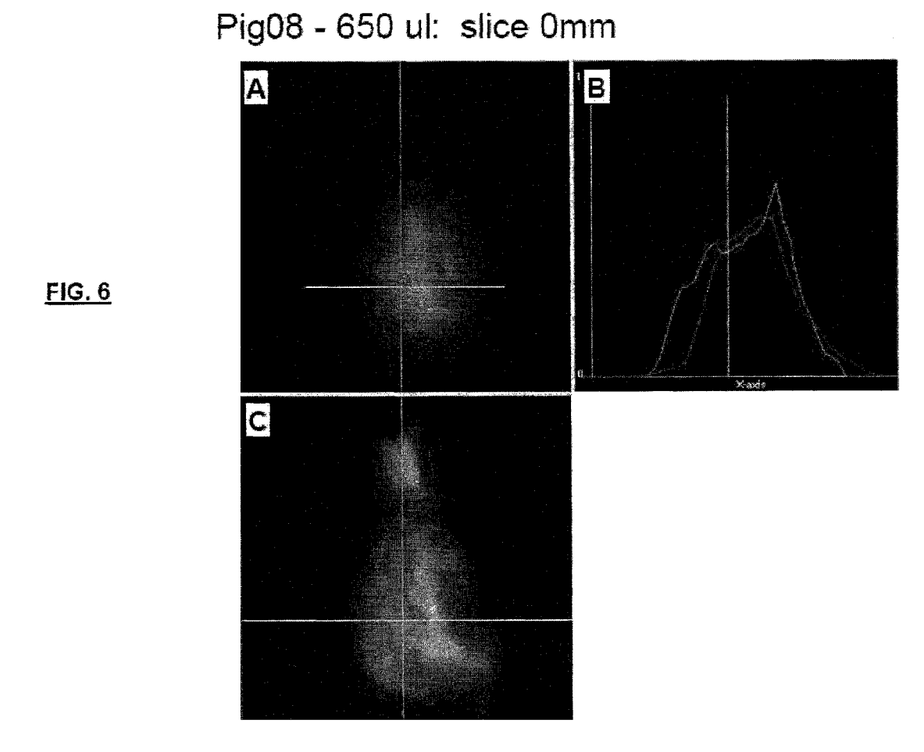
FIG. 6 shows the measured distribution (C) compared with simulation (A) wherein the effect of fiber crossings is not taken into account. It is shown on graph (B) that the dimmer curve (simulation) does not match the brighter curve (measured).
Figure 7:
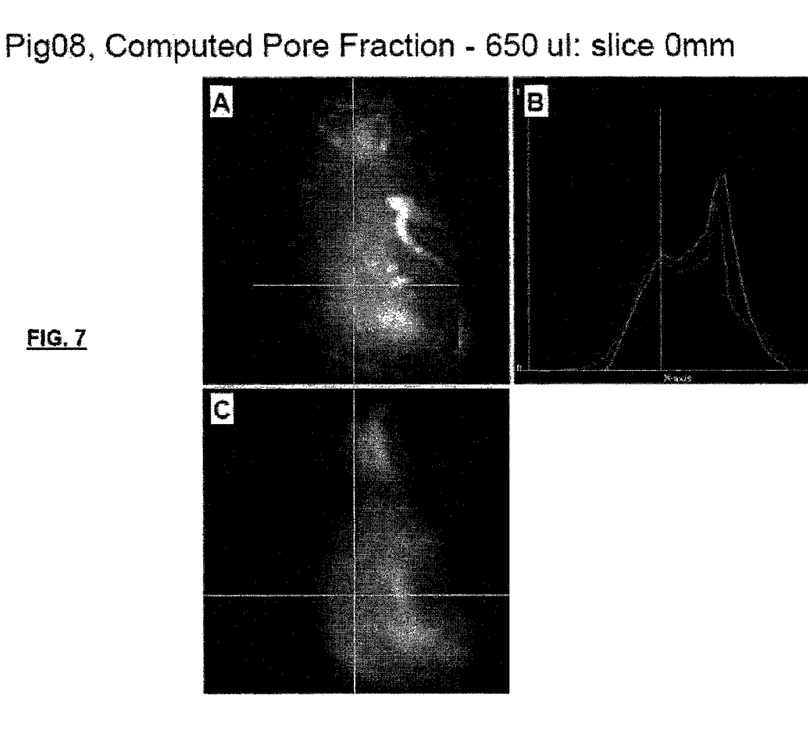
FIG. 7 shows the measured distribution (C) compared with simulation (A) wherein the effect of fiber crossings is taken into account. It is shown on graph (B) that the dimmer curve (simulation) matches the brighter curve (real).
Figure 8:
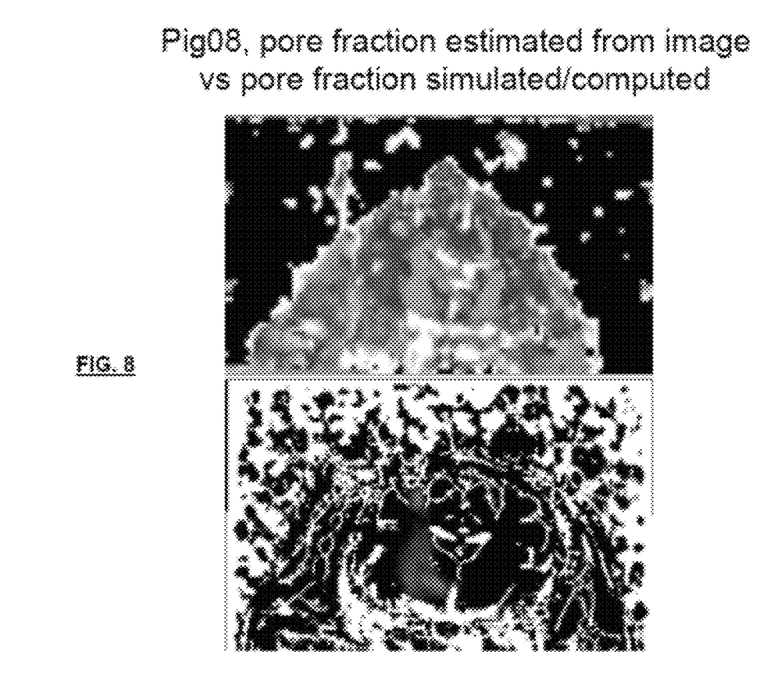
FIG. 8 shows the pore fraction estimated from an image vs. a simulated/computed pore fraction.
Figure 9:
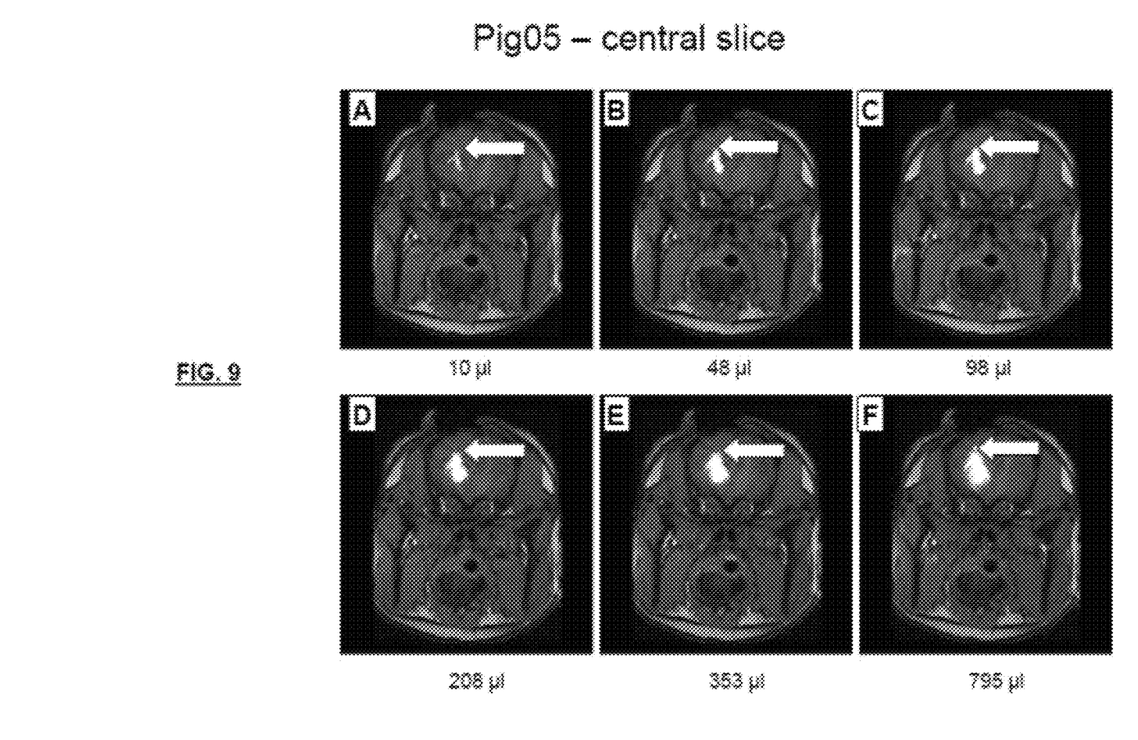
FIG. 9 shows an MRI slice of a pig showing infusion into the pig at various time points into the infusion (respective volumes infused given below the pictures). Dim areas in the distribution indicate regions that are not expanded by the infused fluid and act as a barrier or "bottleneck" for the infusion (indicated by white arrow). Note that in FIG. 9A the point that does not expand at the following
Figure 10:
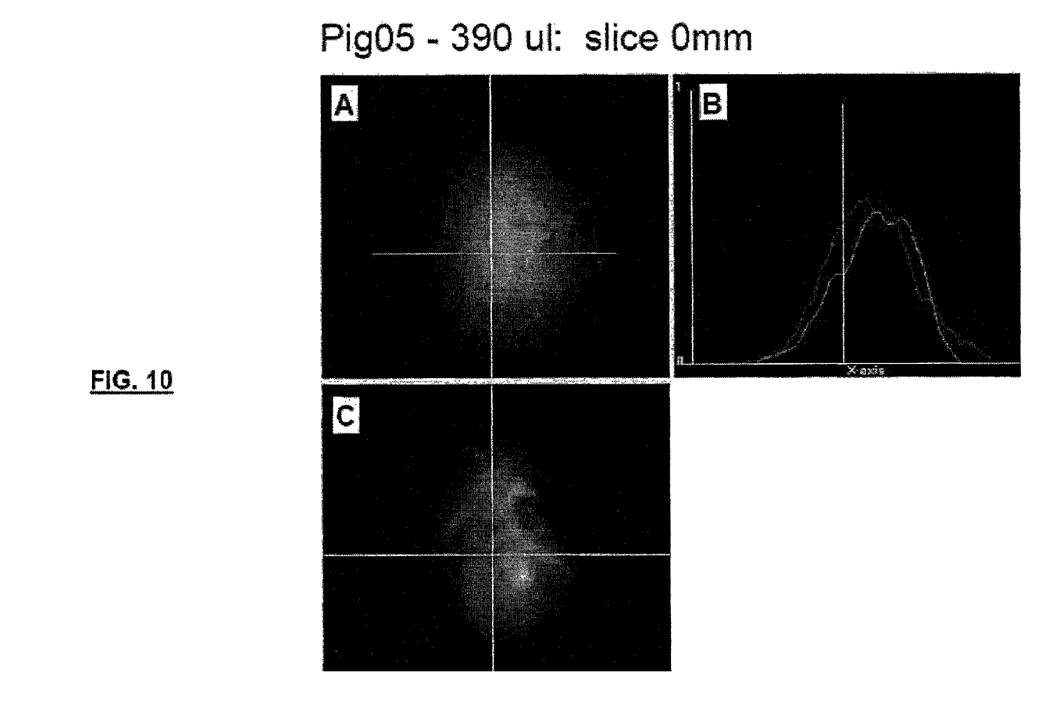
FIG. 10 shows a measured distribution (C) compared with simulation (A) wherein the effect of fiber crossings is not taken into account. It is shown on the graph (B) that the red curve (simulation) does not match the green curve (measured).
Figure 11:
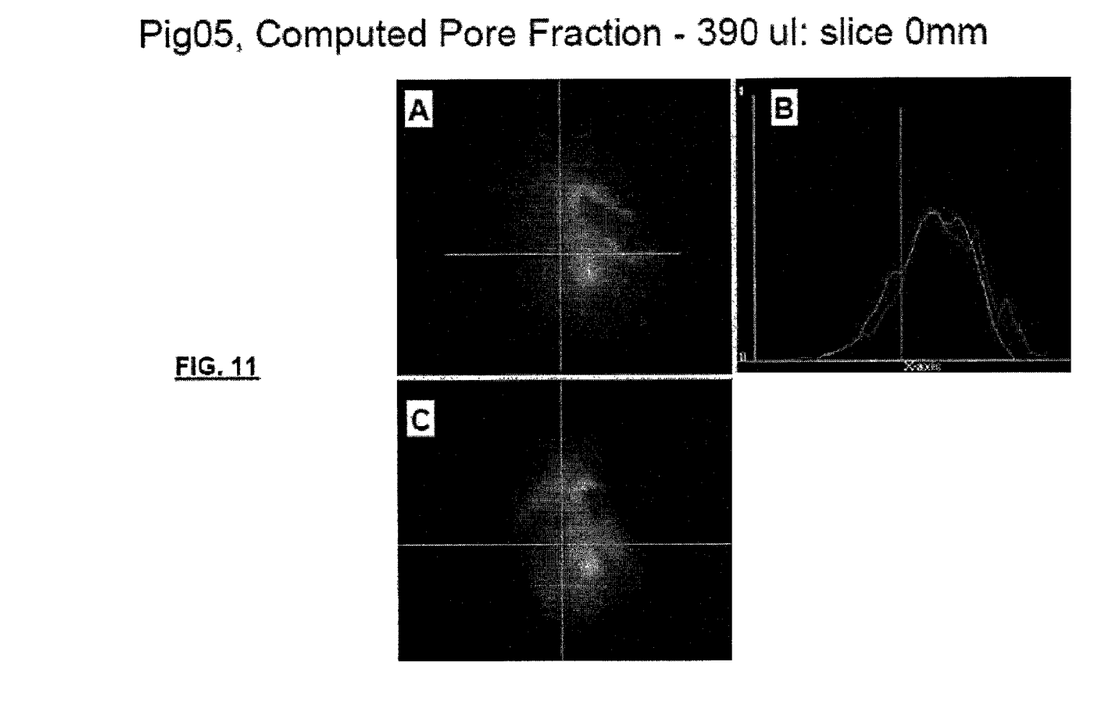
FIG. 11 shows a measured distribution (C) compared with simulation (A) wherein the effect of fiber crossings is taken into account. It is shown on the graph (B) that the red curve (simulation) matches the green curve (measured).

In terms of the infusion of fluid, it is also obtainable from infusion imaging (for example, imaging of a contrast agent that is infused or co-infused into tissue as in FIGS. 1-3) that unexpanded tissue volumes can change the flow dynamics of fluid distribution. For example, because tissue volumes do not expand, the velocity of the fluid is higher at such "bottlenecks" than in other regions that are susceptible to the expansion of the interstitial spaces. Hence, the knowledge of possible expansions can be used to correctly estimate local variations of fluid velocities. This knowledge can be taken into account to improve the pre-infusion simulation of expected fluid distributions.

An exemplary flow chart of an embodiment of a method according to the invention would be as follows:
1. Perform MR imaging to obtain the Diffusion Tensor (DTI) in tissue;
2. Perform MR imaging to obtain intravoxel fiber directions;
3. Perform MR imaging to obtain proton density PD in tissue;
4. Select solvent;
5. Select catheter trajectory, infusion site, and fluid flow rates;
6. Estimate parameters influencing tissue expansion (fiber directionality and entanglement, cross links);
7. Estimate extracellular expansion from phenomenology of cellular and extracellular structures;

8. Check if proposed infusion site and flow rates will allow tissue perfusion of infused fluid. If yes, proceed to 10; if not return to 4;
9. Plan infusion;
10. [Optional] Perform MR imaging to obtain proton density and diffusion tensor during infusion;
11. Observe extracellular volume fraction, and compare with predictions.
12. Refine predictions and return to 10;
13. When predictions are satisfactory, plan (and perform) infusion of therapeutic drug.

BRIEF DESCRIPTION OF THE DRAWINGS

The attached figures illustrate various aspects of the invention. They represent Pig Experiments with reference to the infusion of contrast agents using Convection-Enhanced Delivery ("CED").

FIGS. 3B-3F is the crossing point of white matter tracks.

FIGS. 4 and 5 show the infused white matter (bright white in the images), and a gap where there appears to be a white matter crossing. This suggests that something special is going on in this part of the white matter that prevents the pore fraction expansion that most of the white matter undergoes when pressure is applied.

FIGS. 9B-9F is the crossing point of white matter tracks.

DETAILED DESCRIPTION

In the following, methods for predicting a pore fraction are described. In this respect, it is to be noted that such "pore fraction" is a term synonymously used for the term "extracellular volume fraction" as used herein elsewhere.

A. Method for Predicting Pore Fraction Expansion Due to Infusion

It appears that the expansion is highly localized to the white matter, with little observed change in gray matter regions. Second, the expansion appears to be very significant within the white matter, with the exception of the tightly-packed fibers of the corpus callosum. It is fairly uniform where it occurs, with a sharp boundary between the edematous and normal white matter regions.

The location of the expansion due to infusion appears to match the area infused, in regions of white matter. It might appear that it is necessary to estimate the infusion extent before the pore fraction expansion can be estimated. However, it is reasonable to estimate a pore fraction expansion everywhere, as if the infusion covered the entire brain. This will be incorrect where there is no infusate, but there will be no subsequent infusion simulation at these locations anyway. Thus, the pore fraction change corresponds to a correction for edema covering the entire brain. The estimation is done as follows, at every voxel in the imaging volume.

1. Estimate the fraction of unexpanded white matter, $f_{WM}$, Contained in the Voxel.

In one embodiment, the unexpanded white matter fraction can be estimated in an ad hoc fashion, using the fractional anisotropy, FA, of the diffusion tensor. One method is to use a linear ramp: $f_{WM}=FA/FAmax$ for $FA \leq FA_{max}$ and $f_{WM}=1$ when $FA>FA_{max}$. In order to allow a smoother transition, the ramp can be replaced with a sigmoid function:

$$f_{WM}=1/(1+e^{-s(FA-FAmax/2)})$$

This function yields a white matter fraction of 0.5 when $FA=FA_{max}/2$. On either side of this value, the white matter fraction heads asymptotically towards 0 or 1. Parameter s determines the steepness of the approach. We have used s=20, and $FA_{max}=0.4$.

2. Modify the Local Pore Fraction by Proportionally Increasing the Value in Proportion to the Local Unexpanded White Matter Fraction.

In one embodiment, the expanded local pore fraction modification, $\phi_e$, is obtained as a linear combination of the maximally expanded pore fraction, $\phi_{max}$, and the original pore fraction, $\phi$, according to a weighted sum expression:

$$\phi_e = (f_{WM} \cdot \phi_{max}) + (1 - f_{WM}) \cdot \phi$$

We have used a value of 0.6 for $\phi_{max}$.

B. Method for Measuring Change in Pore Fraction Using MRI

There are a number of "proton density weighted" magnetic resonance imaging sequences in which the acquisition parameters can be adjusted to obtain an image in which the image values are nearly proportional to the density of spins in the imaged region, which is approximately a measure of the amount of water contained in the region. It is possible to create a more accurate estimate of this spin density by taking multiple images with varying TR, TE, or flip angle, in order to compensate for the effects of T1 and T2 weighting. Starting with such a proton density weighted image, one can obtain a map of "water fraction" by dividing the proton density image by the constant value of the proton density measured in pure water.

Typical water fractions, w, in normal brain tissue are approximately 0.8 in gray matter, and 0.7 in white matter largely due the volume of myelin covering white matter axons. Typical pore fraction, $\phi$, in normal white and gray matter is approximately 0.2. This extracellular volume is assumed to contain a fraction of water close to 1.0. The remainder of the 0.7-0.8 fraction of water is therefore found in the intracellular space.

The processes of vasogenic edema and infusion-induced edema expand the extracellular volume, thus reducing the density of cells. Assuming the water fills this expanded extracellular space, this water displaces both intracellular water and non-water cellular material proportionally. Thus, the reduction in the intracellular volume fraction should be proportional to the reduction in the non-water fraction. Let $w_0$ and $w$ represent the water fraction before and after the expansion, respectively. These two quantities can be measured (at the appropriate times) from MRI as described above. Let $\phi_0$ and $\phi$ represent the extracellular volume fraction, or pore fraction, before and after expansion, respectively. The proportionality of intracellular volume change to non-water volume change can be described by the following equation:

$$(1-\phi)/(1-\phi_0) = (1-w)/(1-w_0)$$

This expression can be re-written to express the change in pore fraction, $$\Delta\phi = \phi - \phi_0 = (1-\phi_0)(w-w_0)/(1-w_0)$$

This expression requires a measurement of the proton density before and after the expansion. Furthermore, it requires an estimate of the initial pore fraction, $\phi_0$. In normal, unexpanded white matter this can be assumed to be approximately 0.2.

C. Method for Estimating Pore Fraction Using MRI

In some cases, one may not have a pre-expansion measurement of the water fraction, $w_0$, available. Furthermore, there is no direct way to measure the pre-expansion pore fraction, $\phi_0$, from MRI. But because pore fraction expansion is largely restricted to white matter regions, one can use the nominal normal white matter values, $\phi_0 = 0.2$ and $w_0 = 0.7$ for unexpanded white matter. Then, the pore fraction in white matter can be estimated from a single measurement of water fraction using the expression for change in pore fraction as:

$$\phi = 1 - [(1-\phi_0)(1-w)/(1-w_0)]$$

European Patent Application Nos. 07108374.5 and 08155788.6, respectively filed on May 16, 2007 and May 7, 2008, from which priority is claimed, are hereby incorporated herein by reference in their entireties.

What is claimed is:

1. A method for determining an expanded local pore fraction modification $\phi_e$ of tissue, comprising:
   performing Magnetic Resonance Imaging to obtain a diffusion tensor corresponding to the tissue;
   determining a fractional anisotropy FA of the diffusion tensor;
   determining a fraction of unexpanded white matter $f_{WM}$ from the fractional anisotropy FA of the diffusion tensor; and
   determining the expanded local pore fraction modification $\phi_e$ from a combination of a maximally expanded pore fraction $\phi_{max}$, an original pore fraction $\phi$, and the fraction of unexpanded white matter $f_{WM}$.

2. The method according to claim 1, wherein the tissue comprises brain tissue.

3. The method according to claim 1, wherein determining the expanded local pore fraction modification $\phi_e$ from the combination of the maximally expanded pore fraction $\phi_{max}$, the original pore fraction $\phi$, and the fraction of unexpanded white matter $f_{WM}$ includes using a linear combination of the of maximally expanded pore fraction $\phi_{max}$, the original pore fraction $\phi$, and the fraction of unexpanded white matter $f_{WM}$.

4. The method according to claim 1, wherein the fraction of unexpanded white matter $f_{WM}$ is determined from the fractional anisotropy FA and a maximum fractional anisotropy $FA_{max}$ of said diffusion tensor by using one of the following formulae:

$$f_{WM} = FA/FA_{max} \text{ for } FA \leq FA_{max} \text{ and } f_{WM} = 1 \text{ when } FA > FA_{max}, \text{ or}$$

$$f_{WM} = 1/(1 + e^{-s(FA - FA_{max}/2)}).$$

5. The method according to claim 4, wherein a steepness s of the approach is assigned a predetermined value.

6. The method according to claim 5, wherein the predetermined value of s is 20.

7. The method according to claim 4, wherein the maximally fractional anisotropy $FA_{max}$ of said diffusion tensor is assigned a predetermined value.

8. The method according to claim 7, wherein the predetermined value of $FA_{max}$ is 0.4.

9. The method according to claim 1, wherein the expanded local pore fraction modification $\phi_e$ is determined from a combination of the maximally expanded pore fraction $\phi_{max}$, the original pore fraction $\phi$ and the fraction of unexpanded white matter $f_{WM}$ by using the formula:

$$\phi_e = (f_{WM} * \phi_{max}) + (1 - f_{WM}) * \phi.$$

10. The method according to claim 9, wherein the maximally expanded pore fraction $\phi_{max}$ is assigned a predetermined value.

11. The method according to claim 10, wherein the predetermined value of $\phi_{max}$ is 0.6.

12. The method according to claim 9, wherein the original pore fraction $\phi$ is determined from a combination of a pore fraction $\phi_0$ before expansion, a water fraction $w_0$ before expansion and a water fraction $w$ after expansion using the formula $\phi = 1 - [(1-\phi_0)*(1-w)/(1-w_0)]$.

13. The method according to claim 12, wherein the pore fraction $\phi_0$ before the expansion is assigned a predetermined value.

14. The method according to claim 13, wherein the predetermined value of $\phi_0$ is 0.2.

15. The method according to claim 12, wherein the water fraction $w_0$ before expansion and the water fraction w after expansion is obtained from Magnetic Resonance Imaging.

16. Method according to claim 12, wherein the water fraction $w_0$ before expansion is assigned a predetermined value.

17. The method according to claim 16, wherein the predetermined value of $w_0$ is 0.7.

* * * * *